United States Patent [19]

Hara et al.

[11] Patent Number: 5,463,039
[45] Date of Patent: Oct. 31, 1995

[54] METHOD OF PREPARING HETERO-BRANCHED CYCLODEXTRINS

[75] Inventors: Koji Hara; Koki Fujita, both of Yokohama; Nobuhiro Kuwahara, Yokohama; Sumio Kitahata; Kyoko Koizumi, both of Osaka, all of Japan

[73] Assignees: Ensuiko Sugar Refining Co., Ltd., Kanagawa; Osaka-shi; Kyoko Koizumi, both of Osaka, all of Japan

[21] Appl. No.: 263,124

[22] Filed: Jun. 21, 1994

Related U.S. Application Data

[62] Division of Ser. No. 958,579, Oct. 8, 1992, Pat. No. 5,356,884.

[30] Foreign Application Priority Data

Nov. 13, 1991 [JP] Japan ..................... 3-24021

[51] Int. Cl.$^6$ ............... C08B 37/16; C08L 5/16
[52] U.S. Cl. .............. 536/124; 536/103; 435/74; 435/97; 435/101; 435/103
[58] Field of Search ................ 536/103, 124; 435/74, 97, 101, 103; 514/58

[56] References Cited

U.S. PATENT DOCUMENTS

| | | | |
|---|---|---|---|
| 4,668,626 | 5/1987 | Kobayashi et al. | 435/95 |
| 4,871,840 | 10/1989 | Kobayashi et al. | 536/103 |
| 4,910,137 | 3/1990 | Kobayashi et al. | 435/74 |
| 4,931,389 | 6/1990 | Kobayashi et al. | 435/95 |
| 5,196,406 | 3/1993 | Kamei et al. | 514/58 |

FOREIGN PATENT DOCUMENTS 3192101 8/1991 Japan.
2193963 2/1988 United Kingdom.

OTHER PUBLICATIONS

*Chemical Abstracts*, vol. 115, No. 26, Columbus, Ohio, US, Abstract No. 282425j, "Heterosaccharide–modified cyclodextrin manufacture", Abstract for JP–A–3 192 (National Food Research Institute; Ensuiko Sugar Refining Co., Ltd.) 22 Aug. 1991.

Kitahata et al, "Galactosylation of Side Chains ..." Biosci, Biotech, Biochem, 56(2):pp. 242–245 (1992).

Kitahata et al, "Synthesis of 6-0-α-D-Galactosyl ..." Biosci, Biotech, Biochem, 56(9):pp. 1518–1519 (1992).

Lancelon–Pin et al "α–D–Mannosyl and β–D–Galactosyl Derivatives of Cyclodextrins", Tet. Letters 33(22):pp. 3125–3128 (1992).

*Primary Examiner*—Douglas W. Robinson
*Assistant Examiner*—Kathleen Kahler Fonda
*Attorney, Agent, or Firm*—Frishauf, Holtz, Goodman, Langer & Chick

[57] ABSTRACT

A method of preparing a hetero-branched cyclodextrin comprising a glucosyl or a maltosyl group side chain and a mannosyl group α-bonded to a hydroxyl group of the glucosyl group or the maltosyl group of the side chain, the method involving reacting a liquid containing a branched cyclodextrin having a glucosyl or maltosyl group as the side chain and an α-mannosyl compound with an α-mannosyl transfer enzyme.

8 Claims, 8 Drawing Sheets

G : Glucosyl Group
Man : Mannosyl Group

METHOD OF PREPARING HETERO-BRANCHED CYCLODEXTRINS

This is a division of application Ser. No. 07/958,579 filed Oct. 8, 1992, now U.S. Pat. No. 5,356,884 issued Oct. 18, 1994.

FIELD OF THE INVENTION

The present invention relates to novel hetero-branched cyclodextrins and a method of preparing them. More precisely, it relates to novel hetero-branched cyclodextrins each having a glucosyl or maltosyl group as the side chain and having a mannosyl group α-bonded to the side chain., and to a method of preparing said novel hetero-branched cyclodextrins to be effected by transglycosylation.

BACKGROUND OF THE INVENTION

A cyclodextrin (hereinafter referred to as "CD") is a cyclic dextrin comprising plural glucose residues as bonded to each other by α-1,4-bonding. α,β- and γ-CDs are well known, each comprising 6, 7 and 8 glucose residues, respectively. Recently, for the purpose of improving (or elevating) the solubility of CDs, branched CDs each having a glucosyl or maltosyl group bonded thereto by α-1,6-bond have been prepared.

Such CDs and branched CDs have a cavity in the molecule and the inside of the cavity is hydrophobic. Therefore, they have an including function and have a property of including various oily substances therein. Since CDs and branched CDs have such a property, they are widely used in various fields of food industry, cosmetic industry, drug industry etc.

Recently, in the field of drug industry, saccharides have been noted to have specific cell recognizability, and for the purpose of reducing the influences of the side effects of drugs, a study of utilizing such saccharides as a sensor to the target cells for a drug carrier in a drug delivery system has been made. Mannose is well known to have strong affinity to various parts in living bodies.

Under the situation, the present inventors tried to synthesize hetero-branched CDs by transferring a mannosyl group to a branched CD, for the purpose of applying the including function of branched CDs and the characteristic of mannose to a drug delivery system. As a result, they have found that various commercial α-mannosidase are usable for producing hetero-branched glucosyl or maltosyl CDs in which a mannosyl group has been α-bonded by a transfer action to the side chain of glucosyl-α, β and γCD (hereinafter referred to as G1-αCD, G1-βCD and G1-γCD, respectively) or maltosyl-α, β and γCD (hereinafter referred to as G2-αCD, G2-βCD and G2-γCD, respectively) from an α-mannosyl compound. They have further found that α-mannosidase derived from Jack beans (*Canavalia ensiformis*) is usable for preferentially producing a hetero-branched CD in which one mannosyl group is transferred by α-1,6-bonding to the glucosyl group of the side chain of G1-βCD or to the non-reducing terminal glucosyl group of the maltosyl group of the side chain of G2-αCD. On the basis of the findings, they have completed the present invention.

SUMMARY OF THE INVENTION

Specifically, the present invention provides novel hetero-branched CDs each having a glucosyl or maltosyl group as the side chain, in which a mannosyl group is α-bonded to the 6-positioned hydroxyl group of the glucosyl group of the side chain and also provides a method of preparing novel hetero-branched CDs each having a glucosyl or maltosyl group as the side chain and having a mannosyl group as α-bonded to the 6-positioned hydroxyl group of the glucosyl group of the side chain, in which a liquid containing a branched CD and an α-mannosyl compound is reacted with an α-mannosyl transfer enzyme.

DETAILED DESCRIPTION OF THE INVENTION

Figure 1:
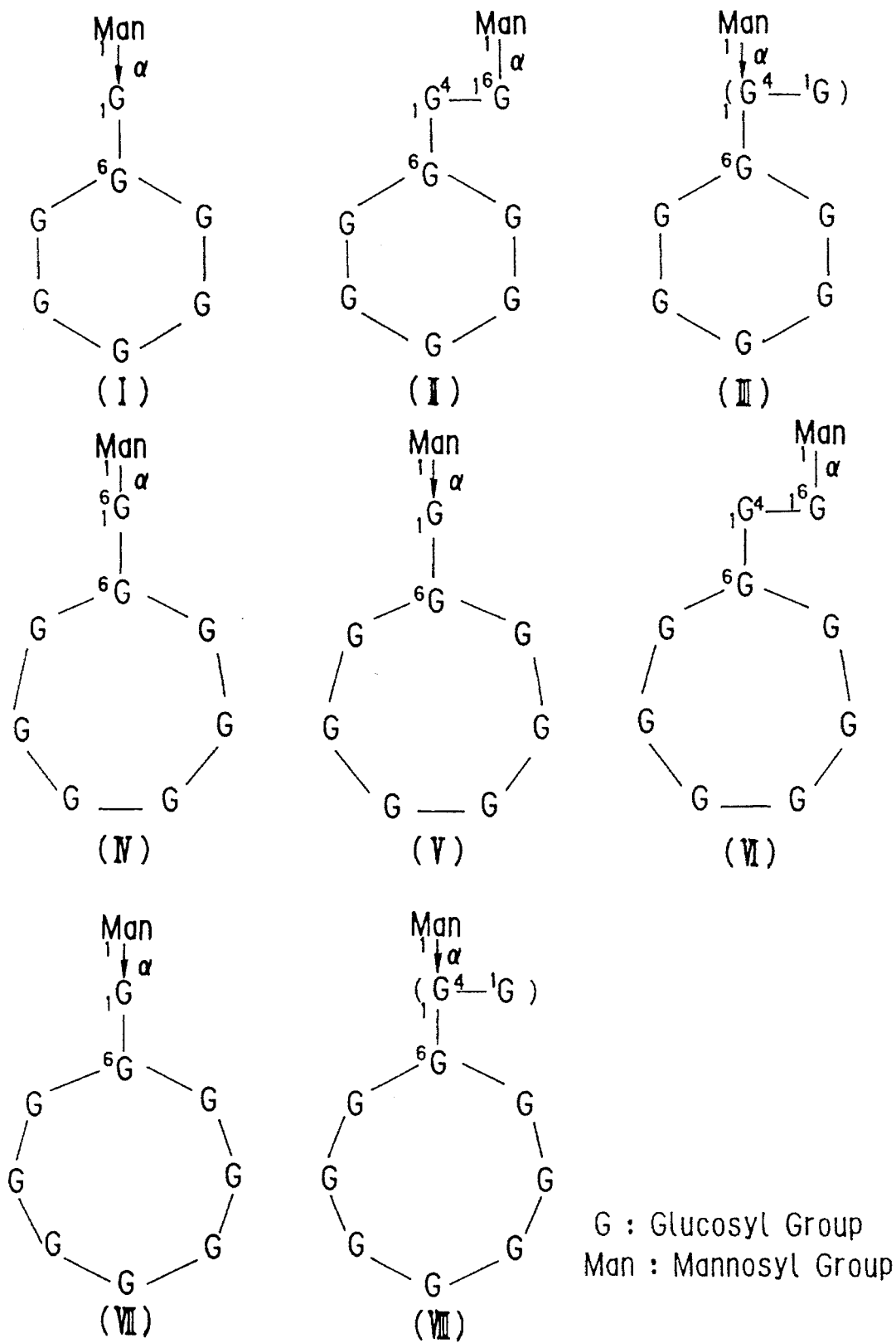
FIG. 1 shows structural formulae of novel hetero-branched CDs of the present invention.

The novel hetero-branched CDs of the present invention may be represented by structural formulae I to VIII as shown in FIG. 1.

The novel hetero-branched CDs of the present invention can be obtained by reacting a liquid containing a branched CD having a glucosyl or maltosyl group as the side chain and an α-mannosyl compound with an α-mannosyl transfer enzyme. The branched CD having a glucosyl or maltosyl group as the side chain, as referred to herein, includes G1-αCD, G1-βCD, G1-γCD, G2-αCD, G2-βCD, G2-γCD, and mixtures of them.

The α-mannosyl compound to be used in the present invention (hereinafter referred to as a "mannosyl donor") includes, for example, α-mannosyl residue-containing glycosides, oligosaccharides or polysaccharides, such as methyl α-mannoside, phenyl α-mannoside, para-nitrophenyl α-mannoside, α-mannooligosaccharides, as well as partial decomposed products of them and mixtures of them.

The α-mannosyl transfer enzyme to be used in the present invention may be anyone which may decompose a mannosyl donor to thereby transfer the resulting α-mannosyl group to the side chain the branched CD having a glucosyl or maltosyl group as the side chain to be α-bonded thereto to produce a hetero-branched CD when applied to a liquid containing an α-mannosyl compound and a branched CD having a glucosyl or maltosyl group as the side chain.

α-Mannosyl transfer enzymes usable in the present invention are widely distributed in the natural field. For instance, well known are enzymes derived from plants such as jack beans (*Canavalia ensiformis*) or almonds (*Prunus amygdalus*), enzymes derived from animals such as turban shells (*Turbo cornutus*) or livers (bovine, rat, human) as well as enzymes derived from microorganisms such as *Arthro-* bacter aurescence and Aspergillus niger.

In the reaction system of the present invention, the liquid (aqueous solution or suspension) containing a branched CD having a glucosyl or maltosyl group as the side chain and a mannosyl donor desirably contains the branched CD in a concentration of approximately from 1 to 100% (W/W) and the mannosyl donor in a concentration of approximately from 1 to 50% (W/W), and the proportion (by weight) of the mannosyl donor to the branched CD is suitably within the range of approximately from 0.1/1 to 50/1, preferably approximately from 0.3/1 to 2/1, though varying in accordance with the kind of the mannosyl donor used.

The pH value of the reaction liquid may be from 3 to 10, preferably from 4 to 9; and the reaction temperature is suitably adjusted to the range of from 20° to 70° C., preferably from 30° to 60° C. The amount of the enzyme to be used has close relation to the reaction time. In general, it may be such that the reaction may finish within 5 to 100 hours, preferably 5 to 20 hours, but is not limited.

The liquid as reacted by the manner mentioned above is then subjected to high performance liquid chromatography, whereupon the transfer product to the branched CD having a glucosyl or maltosyl group as the side chain is isolated. Then, the structure of the transfer product is determined by enzymatic degradation and by analysis of nuclear magnetic resonance (NMR). As a result, they were identified to be hetero-branched CDs having structural formulae I to VIII, respectively, as shown in FIG. 1.

In accordance with the present invention using the transglycosylation of α-mannosidase, novel hetero-branched CDs each having a glucosyl or maltosyl group as the side chain, in which a mannosyl residue is α-bonded to the hydroxyl group of the glucosyl residue of the side chain, may be obtained efficiently. The novel hetero-branched CDs of the present invention are expected to be utilized widely in various fields of drugs, foods and cosmetics.

The present invention will be explained in more detail by way of the following examples, which, however, are not intended to restrict the scope of the present invention.

EXAMPLE 1

Figure 2:
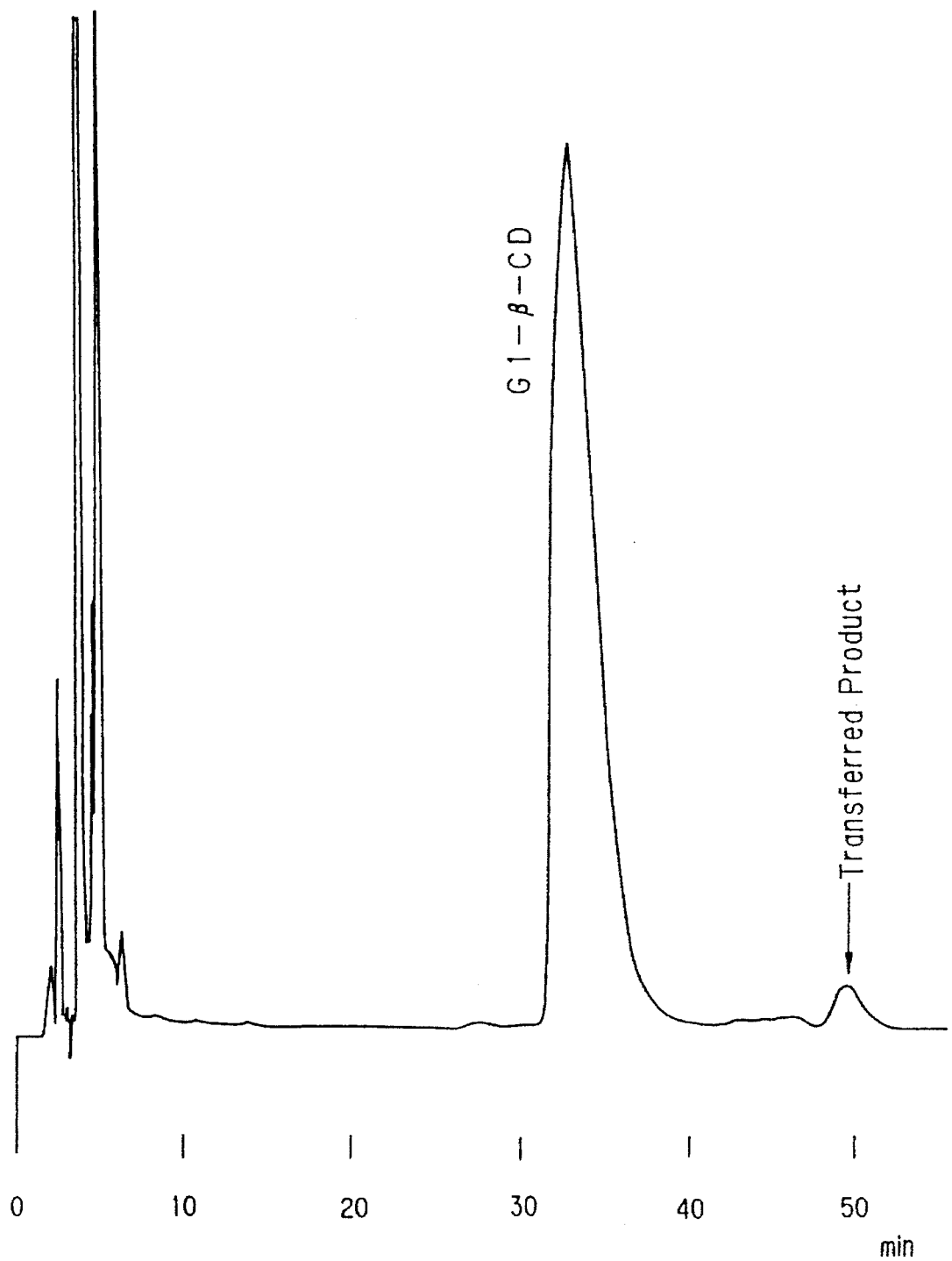
FIG. 2 shows high performance liquid chromatogram of the transfer product of Example 1.
Figure 3:
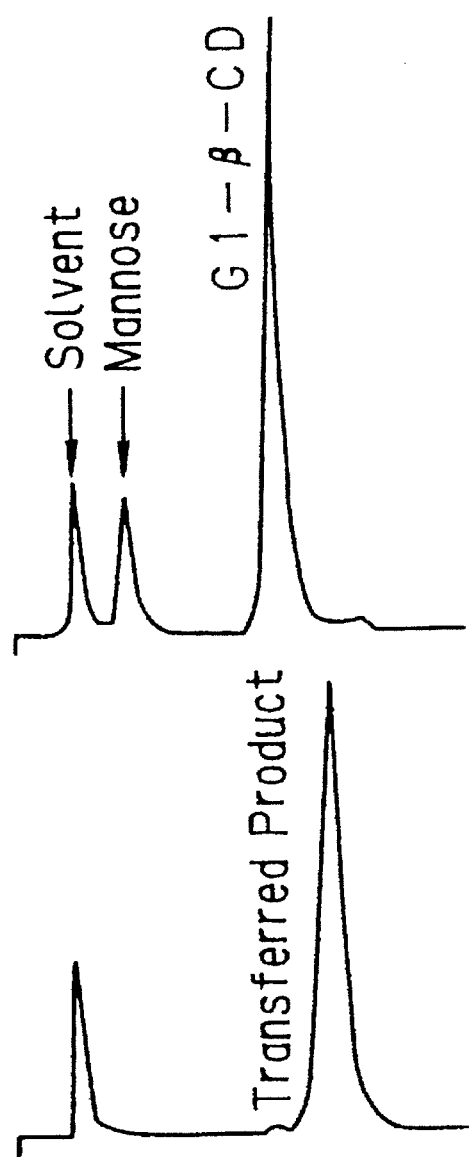
FIG. 3 shows high performance liquid chromatogram of the hydrolyzates from the transfer product of Example 1, as decomposed with α-mannosidase from jack beans (*Canavalia ensiformis*).

(1) Transfer Reaction:
Three grams(3 g) of methyl α-mannoside and 3 g of G1-βCD were dissolved in 10 ml of 50 mM acetate buffer (pH 2.5), and 25 units of α-mannosidase from jack beans (*Canavalia ensiformis*) (product by Sigma Co.) was added thereto and reacted at 40° C. for 20 hours. A part of the reaction mixture was analyzed by high performance liquid chromatography to give the result shown in FIG. 2.

After the reaction, the enzyme used was inactivated under heat and the resulting reaction mixture was subjected to high performance liquid chromatography to isolate 80 mg of the transfer product.

Figure 4:
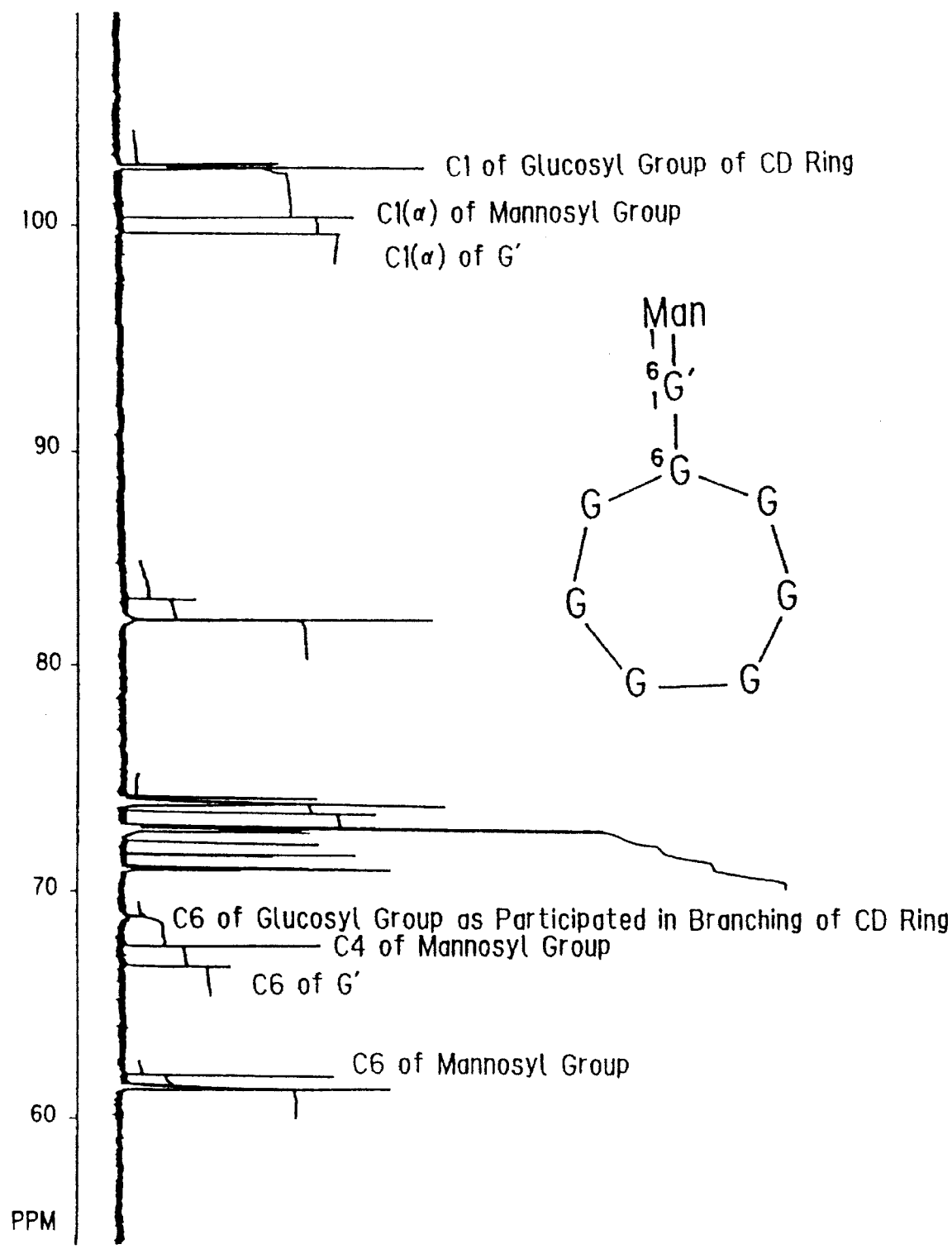
FIG. 4 shows $^{13}$C-NMR spectrum of the transfer product as isolated in (1) of Example 1.

(2) Analysis of Structure:
The transfer product as isolated in the previous (1) was completely hydrolyzed into the same molar amounts of mannose and G1-βCD with α-mannosidase from jack beans (*Canavalia ensiformis*). By $^{13}$C-NMR analysis, the product was identified to be a compound in which a mannosyl residue was α-bonded to the 6-positioned hydroxyl group of the glucosyl residue of the side chain of G1-βCD (having structural formula IV in FIG. 1), as shown in FIG. 4.

EXAMPLE 2

Figure 5:
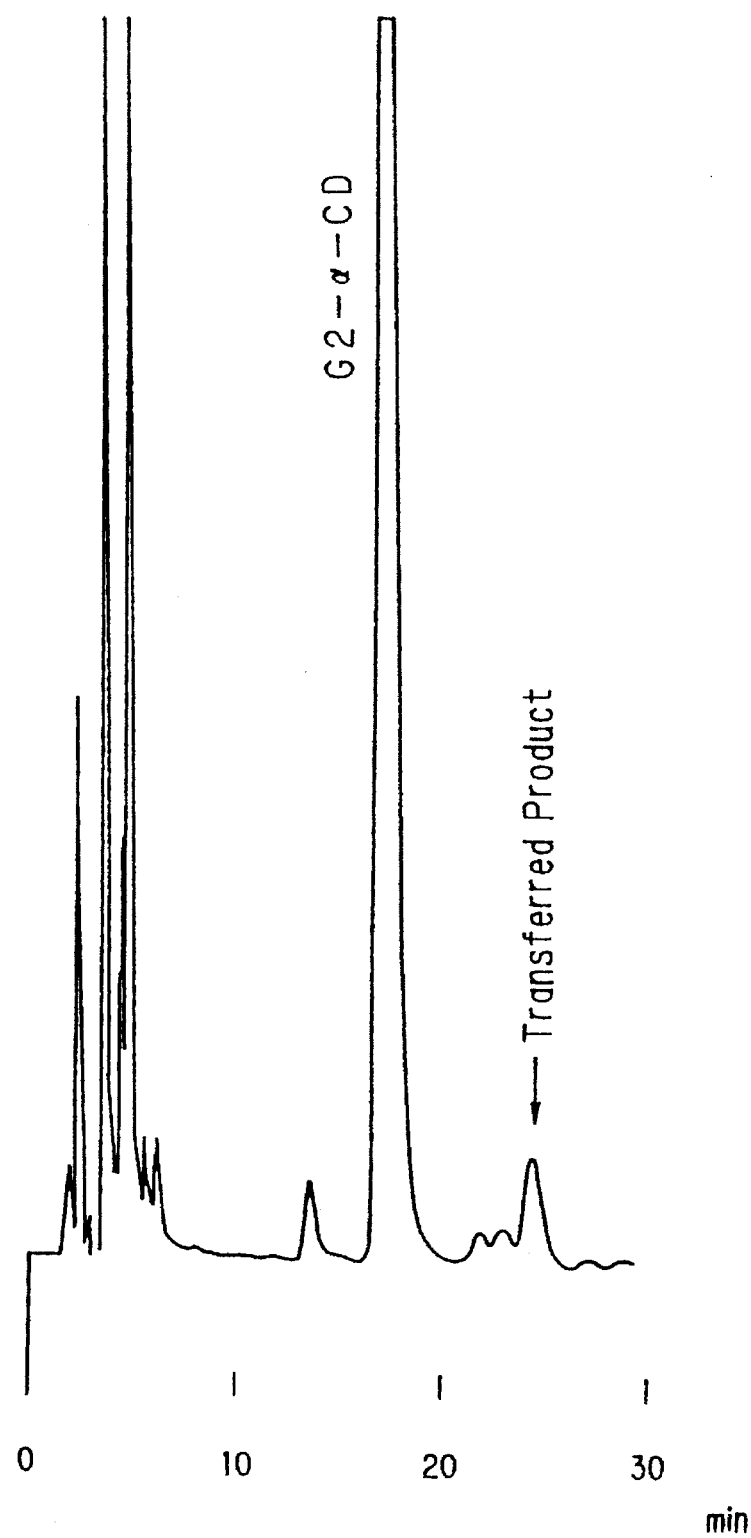
FIG. 5 shows high performance liquid chromatogram of the transfer product of Example 2.

(1) Transfer Reaction:
Three grams of methyl α-mannoside and 3 g of G2-αCD were dissolved in 10 ml of 50 mM acetate buffer (pH 4.5), and 25 units of α-mannosidase from jack beans (*Canavalia ensiformis*) (product by Sigma Co.) was added thereto and reacted at 40° C. for 20 hours. A part of the reaction mixture was analyzed by high performance liquid chromatography to give the result shown in FIG. 5.

After the reaction, the enzyme used was inactivated under heat and the resulting reaction mixture was subjected to high performance liquid chromatography to isolate 57 mg of the transfer product.

Figure 6:
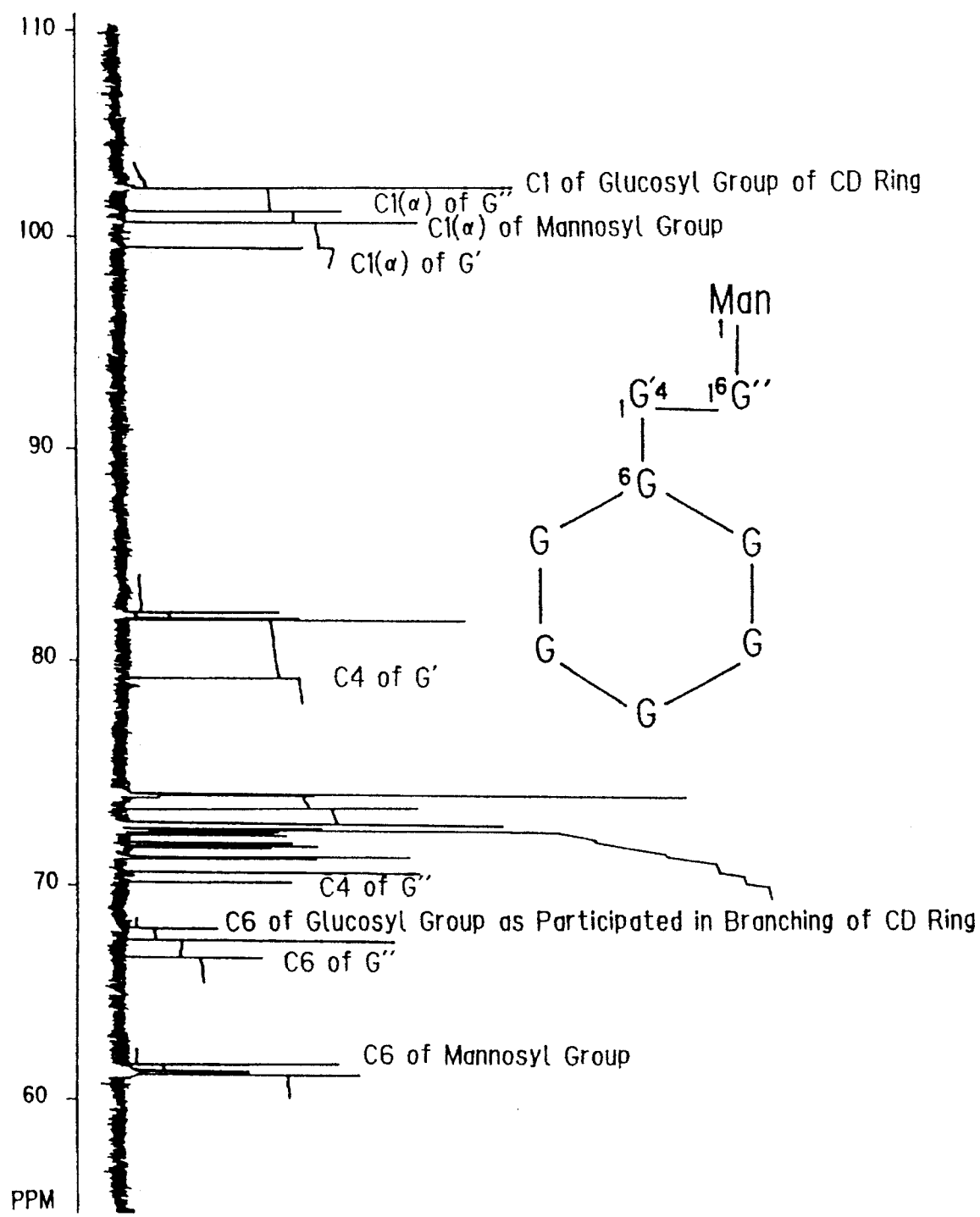
FIG. 6 shows $^{13}$C-NMR spectrum of the transfer product as isolated in (1) of Example 2.

(2) Analysis of Structure:
The transfer product as isolated in the previous (1) was completely hydrolyzed into the same molar amounts of mannose and G2-αCD with α-mannosidase from jack beans (*Canavalia ensiformis*). By $^{13}$C-NMR analysis, the product was identified to be a compound in which a mannosyl group was α-bonded to the 6-positioned hydroxyl group of the non-reducing or reducing terminal glucosyl residue of the maltosyl group of the side chain of G2-αCD (having structural formula II in FIG. 1), as shown in FIG. 6. In the same reaction of using α-galactosidase in place of α-mannosidase, a compound having a galactosyl residue α-bonded to the 6-positioned hydroxyl group of the non-reducing terminal glucosyl residue of the maltosyl group of the side chain of G2-αCD was obtained, which was identified by methylation analysis. Accordingly, also in the case, the maltosyl group may be considered to be α-bonded to the 6-positioned hydroxyl group of the non-reducing terminal glucosyl residue of the maltosyl group.

EXAMPLE 3

(1) Transfer Reaction:
One g of phenyl α-mannoside and 2 g of G1-αCD were dissolved in 10 ml of 50 mM acetate buffer (pH 6.0), and 20 units of α-mannosidase from almonds (*Prunus amygdalus*) (product by Sigma Co.) was added thereto and reacted at 40° C. for 1 hours.

After the reaction, the enzyme used was inactivated under heat and the resulting reaction mixture was subjected to high performance liquid chromatography to isolate 15 mg of the transfer product.

Figure 7:
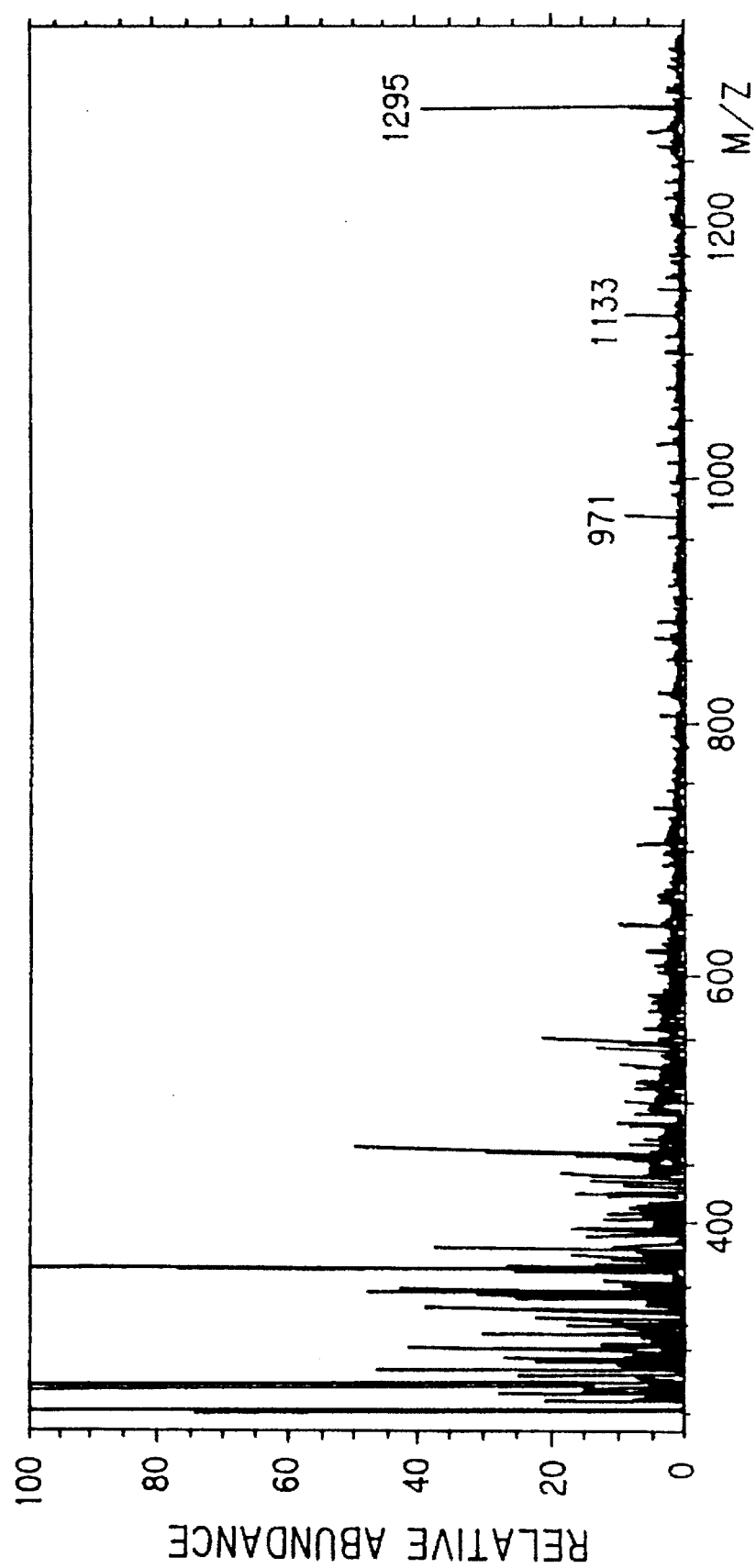
FIG. 7 shows FAB-MS of the transfer product as isolated in (1) of Example 3.

(2) Analysis of Structure:
The transfer product as isolated in the previous (1) was completely hydrolyzed into the same molar amounts of mannose and G1-αCD with α-mannosidase from almonds (*Prunus amygdalus*). Further, it was found, that, by FAB-MS analysis, the molecular weight of the transfer product was 1296 as shown in FIG. 7. This transfer product was also identified to be a compound in which a mannosyl group was bonded to the glucosyl group of the side chain of G1-αCD, since this product has a peak at 971 (see Carbohydrate Research, 215(199)127–136). Therefore, the transfer product as isolated in the previous (1) was identified to be a compound in which a mannosyl residue was transferred and α-bonded to the hydroxyl group at any of C2-, C3-, C4- or C6-position of the glucosyl group of the side chain of G1-αCD (having structural formula I in FIG. 1).

EXAMPLE 4

(1) Transfer Reaction:

One g of phenyl α-mannoside and 2 g of G2-βCD were dissolved in 10 ml of 50 mM acetate buffer (pH 6.0), and 20 units of α-mannosidase from almonds (*Prunus amygdalus*) (product by Sigma Co.) was added thereto and reacted at 40° C. for 1 hour. After the reaction, the enzyme used was inactivated under heat and the resulting reaction mixture was subjected to high performance liquid chromatography (HPLC) to isolate 20 mg of the transfer product.

Figure 8:
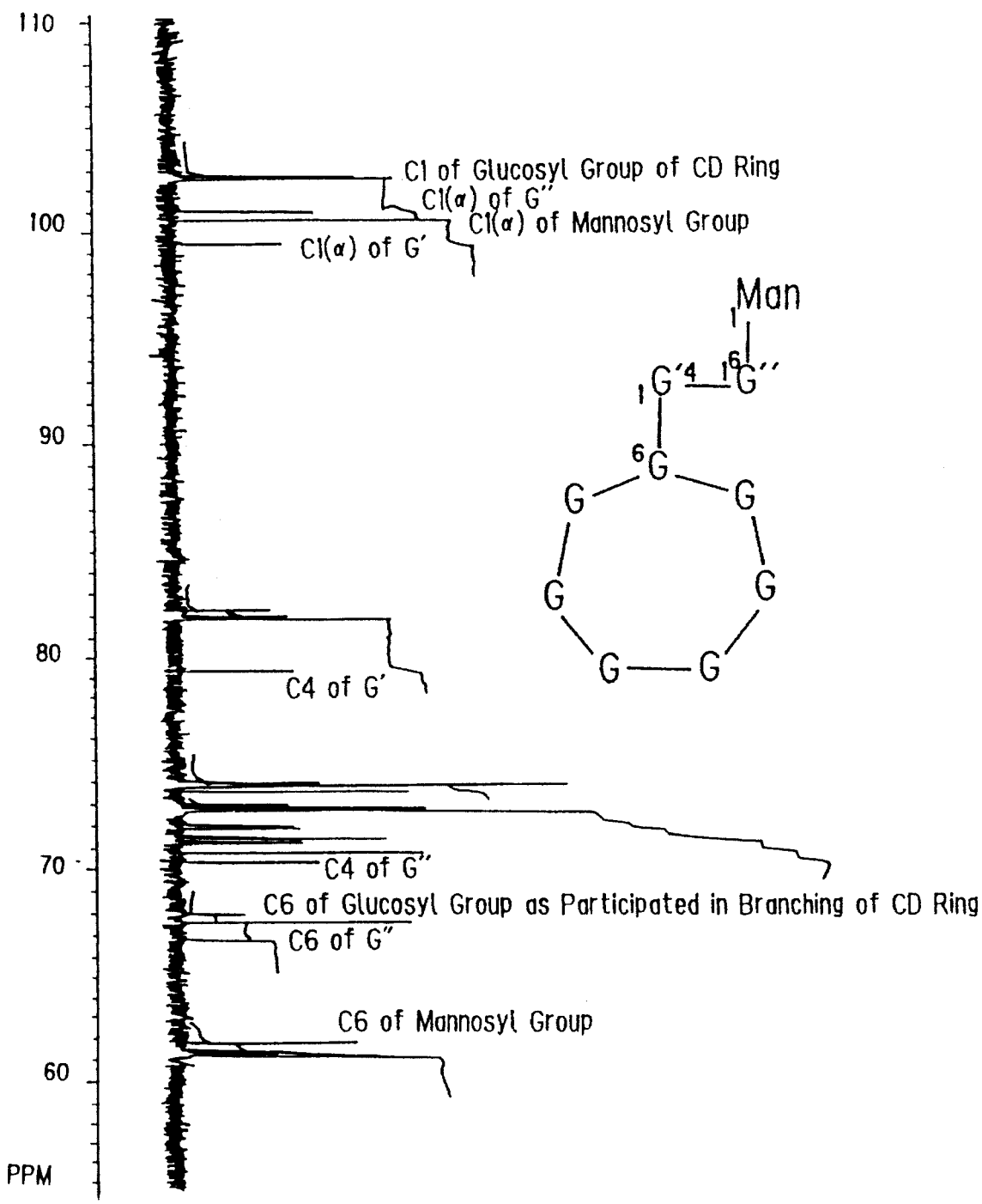
FIG. 8 shows $^{13}$C-NMR spectrum of the transfer product as isolated in (1) of Example 4.

(2) Analysis of Structure:

The transfer product as isolated in the previous (1) was completely hydrolyzed into the same molar amounts of mannose and G2-β CD with α-mannosidase from almonds (*Prunus amygdalus*). From $^{13}$C-NMR analysis, this product was identified to be a compound in which a mannosyl group was α-bonded to the 6-positioned hydroxyl group of the non-reducing terminal glucosyl residue of the maltosyl group of the side chain of G2-βCD (having structural formula VI in FIG. 1), as shown in FIG. 8.

EXAMPLE 5

(1) Transfer Reaction:

Five hundred mg of p-nitrophenyl α-mannoside and 1 g of G1-γCD were dissolved in 10 ml of 50 mM acetate buffer (pH 4.0), and 20 units of α-mannosidase from turban shells (*Turbo cornutus*) (product by Sigma Co.) was added thereto and reacted at 40° C. for 1 hour. After the reaction, the enzyme used was inactivated under heat and the resulting reaction mixture was subjected to high performance liquid chromatography to isolate 15 mg of the transfer product.

(2) Analysis of Structure:

The transfer product as isolated in the previous (1) was completely hydrolyzed into the same molar amounts of mannose and G1- γCD with α-mannosidase from turban shells (*Turbo cornutus*). Further, it was found, that, by FAB-MS analysis, the molecular weight of the transfer product was 1620. This transfer product was also identified to be a compound in which a mannosyl group was bonded to the glucosyl group of the side chain of G1-γCD, since this product has a peak at 1295 (see Carbohydrate Research, 215(1991)127–136). Therefore, the transfer product as isolated in the previous (1) was identified to be a compound in which a mannosyl group was transferred and α-bonded to the hydroxyl group at any of C2-, C3-, C4- or C6-position of the glucosyl group of the side chain of G1-γCD (having structural formula VII in FIG. 1).

EXAMPLE 6

(1) Transfer Reaction:

Five hundred mg of p-nitrophenyl α-mannoside and 1 g of G2-γCD were dissolved in 10 ml of 50 mM acetate buffer (pH 2.0), and 20 units of α-mannosidase from turban shells (*Turbo cornutus*) (product by Sigma Co.) was added thereto and reacted at 40° C. for 1 hour. After the reaction, the enzyme used was inactivated under heat and the resulting reaction mixture was subjected to high performance liquid chromatography to isolate 18 mg of the transfer product.

(2) Analysis of Structure:

The transfer product as isolated in the previous (1) was completely hydrolyzed into the same molar amounts of mannose and G2-γCD with α-mannosidase from turban shells (*Turbo cornutus*). Further, it was found, that, by FAB-MS analysis, a molecular weight of the transfer product was 1782. This transfer product was also identified to be a compound in which a mannosyl group was bonded to the mannosyl group of the side chain of G2-γCD, since this product has a peak at 1295 (see Carbohydrate Research, 215(199)127–136). Therefore, the transfer product as isolated in the previous (1) was identified to be a compound in which a mannosyl group was transferred and α-bonded to the hydroxyl group at any of C2-, C3-, C4- or C6-position of the glucosyl group of the side chain of G2-γCD (having structural formula VIII in FIG. 1).

What is claimed is:

1. A method of preparing a hetero-branched cyclodextrin comprising a glucosyl or a maltosyl group side chain and a mannosyl group α-bonded to a hydroxyl group of the glucosyl group or the maltosyl group of the side chain, the method comprising contacting a liquid containing a branched cyclodextrin having a glucosyl or maltosyl group as the side chain and an α-mannosyl compound with an α-mannosyl transfer enzyme under the conditions of a pH of 3 to 10, a temperature of 20° to 70° C. and a contacting time of 5 to 100 hours, and isolating the resulting hetero-branched cyclodextrin.

2. The method according to claim 1, wherein the branched cyclodextrin is selected from the group consisting of glucosyl 1-α cyclodextrin, glucosyl 1-β cyclodextrin, glucosyl 1-γ cyclodextrin, glucosyl 2-α cyclodextrin, glocosyl 2-β cyclodextrin, glucosyl 2-γ cyclodextrin and mixtures thereof.

3. The method according to claim 2, wherein the α-mannosyl compound is selected from the group consisting of methyl α-mannoside, phenyl α-mannoside, para-nitrophenol α-mannoside, α-mannooligosaccharide and mixtures thereof.

4. The method according to claim 3, wherein the α-mannosyl transfer enzyme is α-mannosidase derived from jack beans, almonds, turban shells, liver or microorganisms.

5. The method according to claim 4, wherein said liquid contains the branched cyclodextrin and the α-mannosyl compound, and the weight ratio of the α-mannosyl compound to the branched cyclodextrin is 0.1/1 to 50/1.

6. The method according to claim 5, wherein the weight ratio of the α-mannosyl compound to the branched cyclodextrin is 0.3/1 to 2/1.

7. The method according to claim 6, wherein the method is carried out at a pH of 4 to 9, a temperature of 30° to 60° C. and a reaction time of 5 to 20 hours.

8. The method according to claim 7, wherein the hetero-branched cyclodextrin is selected from the group consisting of

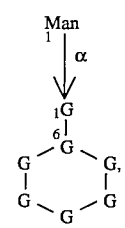
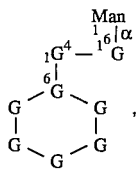
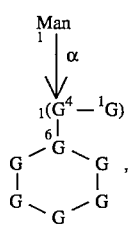
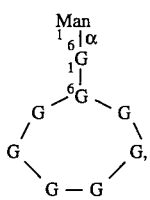
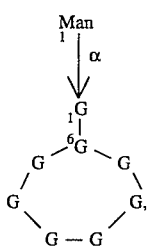
-continued
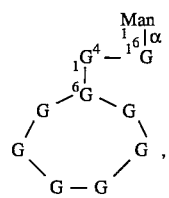
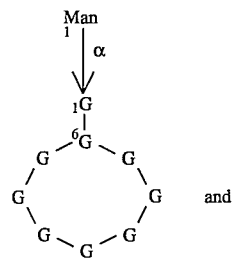 and
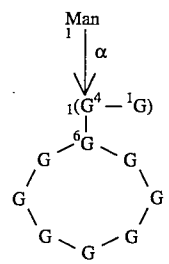
wherein G is a glucosyl group and Man is a manosyl group.
* * * * *

UNITED STATES PATENT AND TRADEMARK OFFICE
CERTIFICATE OF CORRECTION

PATENT NO. : 5,463,039
DATED : October 31, 1995
INVENTOR(S) : HARA et al

It is certified that error appears in the above-indentified patent and that said Letters Patent is hereby corrected as shown below:

Title page, left column, [30], under Foreign Application Priority Data, replace "3-24021" with --3-324021--.

Signed and Sealed this

Twenty-fourth Day of December, 1996

Attest:

BRUCE LEHMAN

Attesting Officer

Commissioner of Patents and Trademarks